United States Patent [19]

Fechtig

[11] Patent Number: Plant 6,043

[45] Date of Patent: Oct. 27, 1987

[54] APPLE TREE NAMED PAR-FECT SPUR CRITERION

[76] Inventor: Allen D. Fechtig, 1642 Christmas Tree Dr., Albany, Oreg. 97321

[21] Appl. No.: 783,152

[22] Filed: Oct. 2, 1985

[51] Int. Cl.[4] ..... A01H 5/03

[52] U.S. Cl. ..... Plt./34

[58] Field of Search ..... Plt. 34–35

*Primary Examiner*—Robert E. Bagwill

*Attorney, Agent, or Firm*—Harvey B. Jacobson

[57] ABSTRACT

This invention relates to a new and distinct variety of apple tree (Par-Fect Spur Criterion) characterized by its smaller size and advanced fruit maturity when compared to the non-spurred Criterion.

3 Drawing Figures

SUMMARY OF THE INVENTION

The new variety orginated in 1983 in my orchrads in Albany, Oreg. as a whole tree spur mutation and was first propagated in 1985 in my orchards.

The accompanying drawings are:

DESCRIPTION

Figure 2:
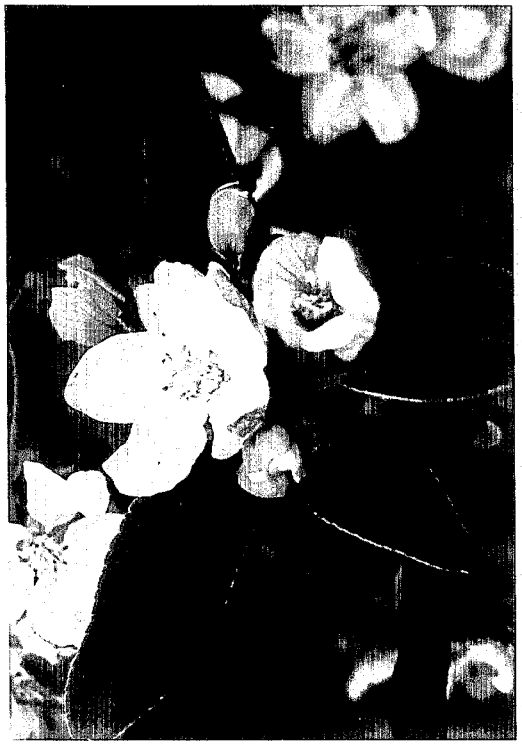
FIG. 2 shows the flower.
Figure 3:
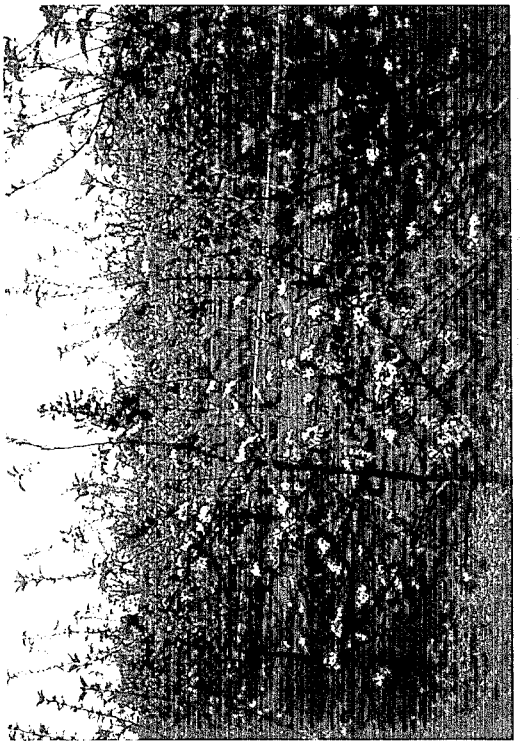
FIG. 3 shows the subject variety at full bloom surrounded by standard Criterion at early bud with an occasional King bloom.
Figure 1:
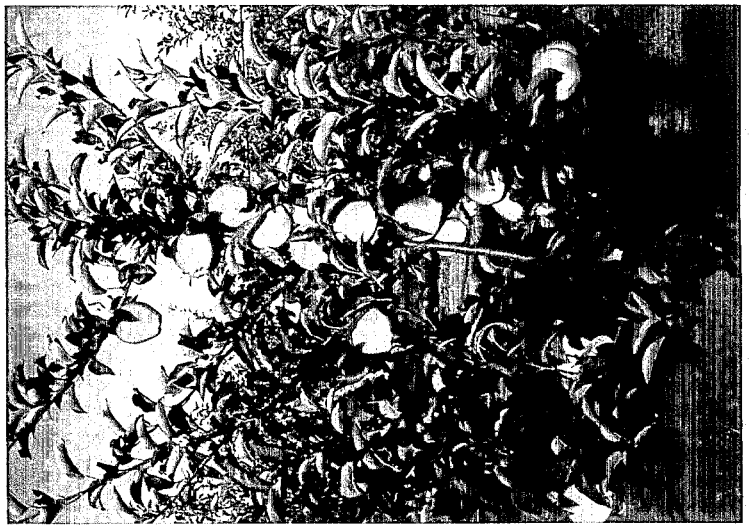
FIG. 1 shows the subject variety with mature fruit.

Tree: Medium size; medium vigor; spreading; low; vase formed; slow growing; hardy; very productive; regular bearer.

*Trunk.*—Stocky to medium; smooth.

*Branches.*—Thick; smooth; shuggy; mature wood brownish grey.

*Lenticels.*—Few; medium.

*Leaves.*—Length 8.5 cm. average; width 6.5 cm. average; large; wide; medium; oval; taper-pointed; thick; dark green; smooth.

*Margin.*—Crenate.

*Petiole.*—Length 3 cm. average; medium; thick.

Flowers: First bloom April 16; 85% full bloom April 28; early; medium; pink bud; pink-white flower; futile.

Fruit: Matures September 26. Length of season April 16–September 26; hangs well; medium; ovate; symmetrical; uniform.

Stem: Medium. Cavity (stem) accute; medium to deep; narrow; smooth; symmetrical.

*Calyx.*—Open; medium.

*Lobes.*—Separated at base; short; medium; acute.

*Basin.*—Shallow; narrow; symmetrical.

*Skin.*—Medium; smooth; waxen; glossy.

*Color.*—Greenish yellow to yellow with Rose Blush.

*Dots.*—Medium; small; russet; areolar.

*Flesh.*—White; firm; crisp; juicy; aromatic.

*Quality.*—Excellent.

*Core.*—Medium; closed.

*Core-lines.*—Meeting.

*Calyx-tube.*—Medium; narrow; conical.

*Seed.*—Small; obtuse; acute.

Use: Dessert; kitchen; market; home.

Keeping quality—Good.

Resistance to:

*Insects.*—Good.

*Disease.*—Good.

Shipping quality: Good.

COMPARISON TO STANDARD NON-SPUR CRITERION

*Leaves.*—The leaves of the subject spur variety and the standard non-spur criterion planted in my orchard are similar in color, shape and size.

*Fruit Buds.*—The fruit buds on the subject spur-Criterion are extremely dense on the central leader and branches. While the standard Criterion trees are primarily tip bearers with fruit buds lacking on the central leader and on the interior portions of the branches.

*Fruit.*—The fruit of the subject spur-Criterion and the standard Criterion appear to be similar in shape, size and color. The maturity in 1984 was 12 days earlier for the spur-Criterion than the fruit produced on the standard Criterion (or non-spur type). The color, maturity, and storage appear to be the same for both the spur and non-spur Criterion. The maturity is 162–164 days after full bloom for both the spur and non-spur. The flavor of the spur and non-spur is the same.

The significant differences between the subject spur Criterion from my orchard and the non-spur Criterion are as follows:

(1) The spur tree is $\frac{2}{3}$–$\frac{3}{4}$ the size of the non-spur (258 cm. vs. 347–374 cm.).

(2) The caliper of the branch wood is thicker.

(3) Fruit spurs are dense on the limbs and central leader on the spur tree, and very sparse and primarily found at the tip of the branches on the non-spur tree.

(a) Central leader of spur Criterion has (15) spurs in 80 cm., while the non-spur Criterion have 2–3 fruit spurs over the 347–374 cm.

(b) Limbs on the spur Criterion tree have spurs starting from 3–14 cm. from the central leader and have from 5–7 spurs the first 40 cm. from the central leader while the non-spur Criterion limbs have fruit located at 76–146 cm (primarily at the tip of the branches).

(4) First bloom and full bloom of the spur tree is 12–14 days advanced over the non-spur criterion.

(5) Fruit maturity is 12–14 days advanced for the spur Criterion when compared to the non-spur Criterion.

Having thus disclosed my invention, I claim:

1. A new and distinct variety of apple tree, substantially as shown and described, characterized particularly by its smaller size and advanced fruit maturity when compared to non-spur Criterion.

* * * * *